United States Patent [19]

Arai et al.

[11] Patent Number: 4,840,778
[45] Date of Patent: Jun. 20, 1989

[54] INORGANIC POLYSILAZANE AND METHOD OF PRODUCING THE SAME

[75] Inventors: Mikiro Arai, Iruma; Takeshi Isoda, Niiza; Takuji Itoh, Sayama, all of Japan

[73] Assignee: Toa Nenryo Kogyo Kabushiki Kaisha, Tokyo, Japan

[21] Appl. No.: 801,884

[22] Filed: Nov. 26, 1985

[51] Int. Cl.$^4$ .................. C01B 33/00; C01B 21/063; C01B 33/06
[52] U.S. Cl. .................... 423/324; 423/344
[58] Field of Search .................. 423/324, 344

[56] References Cited

U.S. PATENT DOCUMENTS

| | | | |
|---|---|---|---|
| 3,853,567 | 12/1974 | Verbeck | 501/92 |
| 4,059,608 | 11/1977 | Calas et al. | 423/324 |
| 4,196,178 | 4/1980 | Iwai et al. | 423/324 |
| 4,310,482 | 1/1982 | Baney | 423/345 |
| 4,387,079 | 6/1983 | Kasai et al. | 423/324 |
| 4,397,828 | 8/1983 | Seyferth et al. | 423/324 |
| 4,482,669 | 11/1984 | Seyferth et al. | 423/324 |

FOREIGN PATENT DOCUMENTS

| | | | |
|---|---|---|---|
| 0038632 | 10/1981 | European Pat. Off. | 423/324 |
| 0145903 | 8/1985 | Japan | 423/344 |
| 1174108 | 8/1986 | Japan | 423/344 |

Primary Examiner—John Doll
Assistant Examiner—Lori S. Freeman
Attorney, Agent, or Firm—Frank J. Jordan; C. Bruce Hamburg; Manabu Kanesaka

[57] ABSTRACT

Novel primarily chain inorganic polysilazanes of average molecular weight of 690 to 2000 are prepared from novel adducts of a halosilane and a base by reacting the adducts with ammonia in unreactive solvents. Silicon nitride is prepared by heating the polysilazanes at 1000° to 1600° C., preferably below 1300° C., most preferably 1000° to 1100° C.

24 Claims, 1 Drawing Sheet

INORGANIC POLYSILAZANE AND METHOD OF PRODUCING THE SAME

BACKGROUND OF THE INVENTION AND RELATED ART STATEMENT

The present invention relates to a process for synthesizing a polysilazane from a halosilane adduct, which may or may not be isolated, to the halosilane adduct, to the polysilazane, and to a method of preparing silicon nitride from the polysilazane.

Sintered silicon nitrides are important high-temperature structural materials for gas turbines and diesel engines because of their excellent high-temperature strength, thermal shock resistance and oxidation resistance. They are also important as high-performance materials for cutting tools, etc., since they contribute to the saving of energy and resources.

The silicon nitrides have been produced by (1) a direct sintering process wherein metallic silicon powder is directly nitrided by heating to 1300° to 1500° C. in a nitrogen or ammonia stream, (2) a silica reduction process wherein silica or a silica-containing substance is reduced with carbon by heating it in a nitrogen atmosphere and silicon thus formed is reacted with nitrogen, (3) a gas-phase synthetic process wherein silicon tetrachloride is directly reacted with ammonia at a high temperature and (4) an imide thermal decomosition process wherein silicon diimide obtained by ammonolysis of silicon tetachloride is heated in a non-oxidizing atmosphere to obtain silicon nitride.

However, the above process (1) requires a long reaction time and complicated heating steps and the resulting silicon nitride comprises mainly rough, $\beta$-type silicon nitride having a high impurity content. The process (2) has defects that the purification of the starting material is difficult, that a long reaction time is required and that the obtained product is a mixture of $\alpha$-type and $\beta$-type silicon nitrides. In the process (3), the resulting silicon nitride is generally amorphous. Though the process (4) has an advantage that $\alpha$-type silicon nitride having a high purity can be produced in a high yield, it has also a disadvantage that, since silicon diimide $[Si(NH)_2]_x$ as a precursor of silicon nitride is insoluble in a solvent, the use thereof is limited in practice.

Recently, a process has been proposed wherein a polysilazane obtained by thermally decomposing an organic polysilazane is heated to 800° to 2,000° C. to form silicon nitride by calcination [see Hajime Saito, "Sen'i Gakkai-shi" Vol. 38, No. 1, pp. 65–72 (1982)]. This process has, however, a defect that silicon carbide and free carbon are formed in addition to silicon nitride.

On the other hand, inorganic polysilazanes soluble in solvents were synthesized by A. Stock et al. in 1921 and it was proved by Seyferth et al. in 1982 that they were useful as precursors of silicon nitride.

However, conventional processes for producing inorganic polysilazanes wherein dichlorosilane having a high vaporizing is used have the following defects: (1) ammonium chloride obtained as the by product and the polysilazane are deposited on the walls of gas tubes and reactors in the reaction apparatus to clog the gas duct, (2) in order to prevent this trouble, the reaction temperature should be kept low to inhibit the scattering of dichlorosilane, and (3) dichlorosilane having a high toxicity and flammability should be kept in a closed vessel at a low temperature. The polysilazane synthesized by the above Stock's process is only an oligomer of the formula: $(SiH_2NH)_n$ in which n is a number of 7 to 8 whichis in the form of a viscous liquid at ambient temperature. The product obtained by the process of D. Seyferth is in the form of an oily liquid having a proton ratio of Si—H/N—H of about 3.3. This product solidifies by heating to about 200° C. or by being left to stand at room temperature for 3 to 5 days. The properties of all of these polysilazanes were insufficient for the precursors of silicon nitride shaped at ambient temperature.

SUMMARY OF THE INVENTION

Objects of the present invention include providing a process for synthesizing an inorganic polysilazane suitable for the production of sintered silicon nitride easily in a high yield and a process for such production of sintered silicon nitride from the inorganic polysilazane.

Other objects of the invention are to provide a high-molecular inorganic polysilazane suitable for the production of shaped silicon nitride and a process for readily synthezing the polysilazane.

Yet another object of the invention is to provide a halosilane adduct, which may or may not be isolated, from which a polysilazane according to the invention may be prepared according to the process according to the invention.

These and other objects and advantages of the invention will be apparent from the following description of the invention.

SUMMARY OF THE INVENTION

Figure 1:
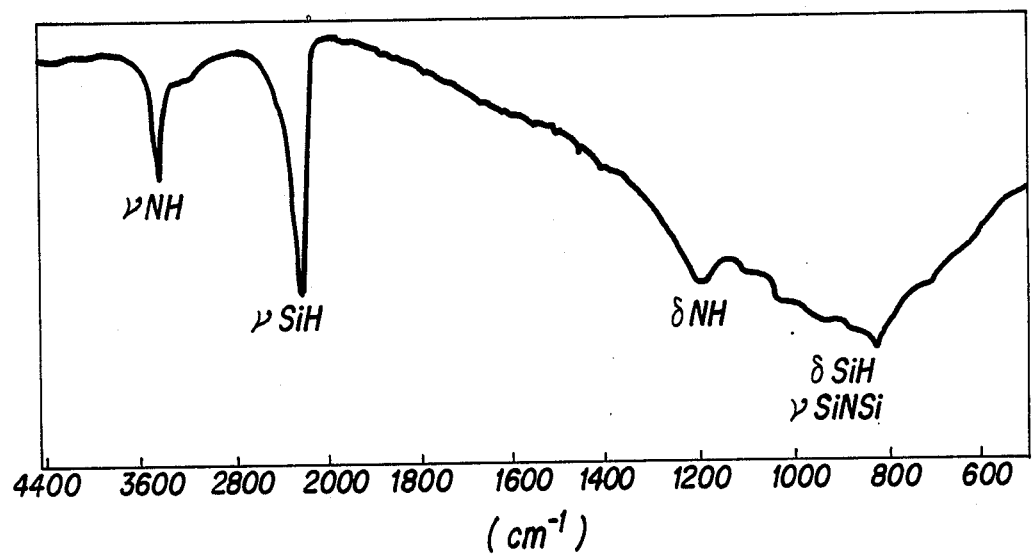
FIG. 1 is an IR spectrum (KBr) of an inorganic polysilazane according to the invention.

According to one aspect of the present invention, there is provided a process for producing an inorganic polysilazane from a halosilane which is characterized in that a step of preparing a halosilane adduct is included in the course of the production of a final product from starting materials.

Inorganic polysilazanes according to the present invention have mainly a skeletal structure of the formula: $(-SiH_2NH-)_n$ wherein n represents a numeral of at least 15 and a molecular weight of at least 690. When said inorganic polysilazane is heat-treated from 1000° C. to 1100° C. in the presence of nitrogen, $\alpha$-type silicon nitride having a high purity can be obtained. Since said polysilazane may be obtained in either a liquid or solid form, it can be used for various purposes could not be attained in the prior art. Namely, it can be used for the production of silicon nitride to be used as an agent for increasing the density of ceramics, bonding agent for ceramic powders and fibers and coating agent for ceramic structures.

The halosilanes used in the present invention include dihalosilanes. Particularly, dihalosilanes of the general formulae: $SiH_2X_2$ and $Si_2H_4X_2$ wherein X represents F, Cl, Br or I are preferred. Among these dihalosilanes, dichlorosilane is particularly preferred in the present invention.

The halosilane adduct formed in the course of the reactions in the present invention may be substantially a reaction intermediate which may be either isolated or not.

The halosilane adduct in the present invention may be formed easily from a halosilane and a base.

The bases usable herein are those inert to reactions other than the formaion of an adduct with the halosilane. Examples of them include tertiary amines (trialkylamines, pyridine, picoline and derivatives of them) and sterically hindering group-containing secondary amines, phosphine, stibine, arsine and derivatives of them (such as trimethylphosphine, dimethylethylphosphine, methyldiethylphosphine, triethylphosphine, trimethylarsine, trimethylstibine, trimethylamine, triethylamine, thiophene, furan, dioxane, selenophene and 1-methylphosphole). Among them, bases having a low boiling point and a basicity lower than that of ammonia are preferred. Preferred examples of such bases include, pyridine, picoline, trimethylphosphine, dimethylethylphosphine, methyldiethylphosphine, triethylphosphine, thiophene, furan, dioxane, selenophene and 1-methylphosphole. Among them, pyridine and picoline are particularly preferred from the viewpoints of handling and economization. The amount of the base used is not critical. An amount larger than the stoichiometrical amount based on the base (including that contained in the adduct), i.e. at least an amount which satisfies a base to halosilane ratio of 2/1 is satisfactory.

The embodiments of the process of the present invention for synthesizing an inorganic polysilazane via the adduct are: (1) a process wherein said halosilane is reacted with a base and the resulting adduct is added to a reaction solvent, (2) a process wherein the halosilane is added to a reaction solvent containing the base and (3) a process wherein the halosilane is added to a mixture of the base and a solvent. The reaction solvent used in this process may be selected from among unreactive solvents over a wide range in which the polysilazane is soluble, disregarding the solubility of the halosilane therein.

The solvents used in the present invention are preferably volatile solvents such as hexane, benzene, pyridine, chloromethane, ether and acetonitrile. Among them, pyridine and chloromethane are particularly preferred.

The process of the present invention for producing a polysilazane via an adduct essentially comprises a reaction of the halosilane adduct with ammonia in an unreactive solvent to carry out the polymerization and, therefore, ammonia is indispensable in the process of the invention. The amount of ammonia used is, however, not critical. It will suffice if ammonia is in excess of halosilane.

As for the reaction conditions in the production of a polysilazane according to the present invention, the reaction time and pressure are not particularly limited, since a high reaction rate can be attained by controlling the reaction temperature in the range of −78° C. to 100° C., preferably −40° C. to 80° C. When the reaction temperature is below −78° C., the yield of the polysilazane soluble in the reaction solvent is reduced, while when it is above 100° C., the formed polysilazane is decomposed again unfavorably.

The polymerzation reaction for forming said polysilazane is carried out preferably in an inert gas atmosphere. The inert gas is preferably nitrogen or argon gas.

By the above-mentioned operation according to the present invention, a substitution reaction proceeds to form a polysilazane which is in the form of a solution in the solvent. An ammonium salt contained as the by-product therein can be separated easily from the polysilazane solution by, for example, filtration. Then, the solvent is removed from the polysilazane solution to obtain an inorganic polysilazane as a colorless, transparent liquid or colorless solid. When the liquid inorganic polysilazane is left to stand at room temperature, a translucent, solid inorganic polysilazane is obtained.

The IR spectrum showed the following (FIG. 1, KBr): 3880 cm$^{-1}$ ($\nu$NH), 2160 ($\nu$SiH), 1190 ($\delta$NH), 1050~800 ($\delta$SiH, $\nu$SiNSi). The $^1$HNMR spectrum showed the following (FIG. 2, CDcl$_3$): $\delta$ 4.72, 4.37ppm(SiH), 1.5(NH). according to the present invention was 59 to 61 wt. % of Si, 31 to 34 wt. % of N and 6.5 to 7.5 wt. % of H as determined by chemical analysis.

The above-mentioned results of the IR spectrum, $^1$H—NMR spectrum and chemical analysis proved that the polysilazane obtained by the process of the present invention had mainly a structure having the following skeleton:

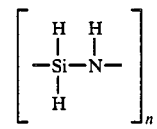

The polysilazane had a molecular weight in the range of 690 to 2000 as determined by a vapor pressure osmometry, corresponding to the degree of polymerization (n) of 15 to 40.

According to the present invention, the polysilazane compound obtained by the above-mentioned process may be heat-treated in the presence of nitrogen to obtain a silicon nitride having a high purity and a proportion of an $\alpha$-type crystal structure of as high as at least 70%. The term "in the presence of nitrogen" herein means that the reaction is carried out in the presence of ammonia alone, nitrogen alone, a mixture of nitrogen and the other gas such as hydrogen, ammonia or argon or a nitrogen-containing cracking gas such as ammonia cracking gas. In case the gaseous mixture is used, it is preferred that nitrogen element is contained therein a large amount, though the proportion thereof is not particularly limited.

Silicon nitride used as a powdery starting material for sintered silicon nitride has preferably a high purity and an $\alpha$-crystal structure in general, since phase transfer of the starting material from $\alpha$ to $\beta$ occurs in the course of the sintering treatment and, consequently, the sinterability is improved and the fibrous texture is developed to form a sintered silicon nitride having a high strength.

To obtain a silicon nitride having an $\alpha$-phase content of at least 70% and a quite excellent sinterability in a high yield from the polysilazane produced by the present invention, the heat treatment should be conducted at a temperature limited within a narrow range of 1000° to 1100° C. However, satisfactorily sinterable silicon nitride will be obtained if the heat treatment temperature is from 1000° to 1600° C. and, especially, below 1300° C.

When the heat treatment temperature is as low as, for example, 500° C. or lower, unreacted chlorine and hydrogen cannot be removed completely and, therefore, the intended silicon nitride contains them unfavorably. When the treatment temperature exceeds 1900° C., formed silicon nitride is dissociated unfavorably. When the polysilazane obtained by the present invention is treated at a temperature of 700° to below 1000° C., a mixture comprising mainly amorphous silicon nitride and silicon is obtained and, when it is treated at above 1600° to 1900° C., β-silicon nitride is obtained as the main product unfavorably.

The heat treatment is generally conducted until the formation of hydrogen as a by-product of heating ceases. The heat treatment time is relatively short at a high temperature and relatively long at a low temperature. To age the crystals, a relatively long heat treatment time is required. Though the time is not particularly limited, it is preferably 8 to 20 h, particularly 10 to 16 h.

In the heat treatment of the polysilazane under nitrogen atmosphere in a furnace according to the present invention, it is desired that the furnace wall is made of a non-oxide materail such as silicon nitride, silicon carbide, tantalum or molybdenum.

A silicon nitride having a high purity (chlorine content of less than 0.001%) and the nitrogen content of at least 39% and comprising at least 70% of the α-crystal structure cannot be obtained unless the conditions are controlled as described above. If necessary, silicon nitride containing an element known to be effective in accelerating the sintering of silicon nitride, such as Mg, Y, Fe or B, can be obtained.

In the production of the inorganic polysilazane from the adduct capable of being present as a stable solid in the reaction solvent and ammonia as substantial starting materials, the defects of the conventional process wherein dichlorosilane is used directly as the starting material, i.e. the scattering of the halosilane and clogging of the reaction apparatus can be overcome. In addition, since (1) the reaction temperature may be elevated because the halosilane is not scattered and (2) the concentration of the halosilane in the reaction mixture may be increased substantially, the rate of the reaction for producing the inorganic polysilazane can be increased. Further, the polymerization reaction of the inorganic polysilazane is facilitated by carrying out the reaction via the adduct and, consequently, the yield and the molecular weight can be improved remarkably. An unreacted adduct can be separated from the resulting inorganic polysilazane by filtration or the like. Thus, the process of the present invention for producing the inorganic polysilazane realizes a high workability and it is far superior to the conventional processes.

According to the process of the present invention, the inorganic polysilazane in a desired state ranging from a viscous, oily product to a glassy product can be obtained as desired. The inorganic polysilazane can be shaped easily, since it is solidified rapidly by removing the reaction solvent. The product thus shaped may be heat-treated to obtain a quite new, shaped silicon nitride. Thus, the present invention is very significant also from this viewpoint.

The following examples will further illustrate the present invention which by no means limit the invention.

EXAMPLE 1

A 300 ml four-necked flask was fitted with a gas-inlet tube, mechanical stirrer and Dewar condenser.

The reactor was purged with dry oxygen-free nitrogen. 150 ml of dry degassed pyridine was placed in the flask and cooled with ice. 16.1 g of dichlorosilane was added thereto over 50 min to form a white, solid adduct ($SiH_2Cl_2 \cdot 2Py$). The reaction mixture was cooled with ice. A mixture of 10.9 g of ammonia purified by passing through a soda lime tube and an active carbon tube and nitrogen gas was introduced thereinto over 1 h.

Figure 2:
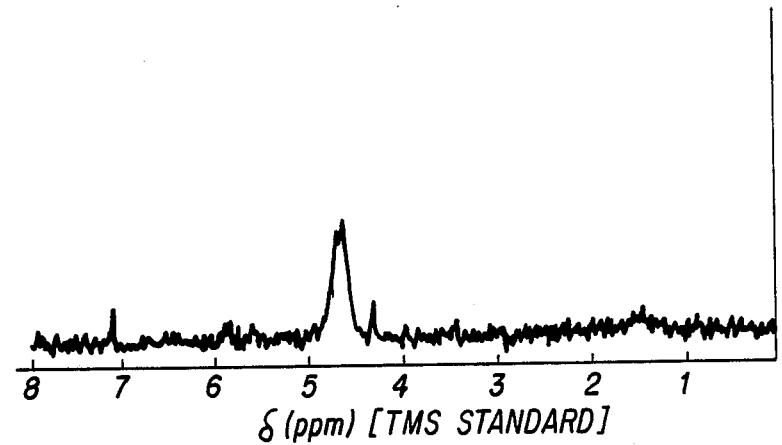
FIG. 2 is a 'HNMR spectrum of the inorganic polysilazane of FIG. 1.

After completion of the reaction, the solid product was removed by centrifugation followed by filtration. The solvent was removed from the filtrate under reduced pressure (50° C., 5 mmHg, 2 h) to obtain 5.52 g of a polysilazane in the form of a glassy solid. This product showed IR and $^1H$—NMR spectra as shown in FIGS. 1 and 2, respectively. In the NMR spectrometry, only the products soluble in the solvent used ($CDCl_3$) were examined. The elementary composition (wt. %) determined by chemical analysis was as follows: Si/N/H=61.0/31.0/7.0. The molecular weight of the product determined by vapor pressure osmometry was 2000. The yield was as high as 77%. The yield and molecular weight of polysilazane produced by a process disclosed in the specification of Japanese Patent Application No. 80109/83 were 45% and 1390, respectively. It was thus proved that both the yield and the molecular weight of the product were improved by the process of the present invention.

EXAMPLE 2

A dropping funnel was attached to the apparatus used in Example 1. 52 ml of dry degassed pyridine and 40 ml of dichloromethane were placed therein. 110 ml of dry degassed dichloromethane was placed in the four-necked flask. After cooling with ice, 16.1 g of dichlorosilane was added thereto. The pyridine solution obtained as above was added dropwise to dichlorosilane over 20 min under cooling with ice. A mixture of 10.9 g of purified ammonia and nitrogen gas was introduced into a milky reaction mixture under vigorous stirring over 1 h. In the course of the reaction, no dust was observed in the gas duct at all.

The reaction mixture was treated in the same manner as in Example 1 to obtain 4.92 g of oily polysilazane having an extremely high viscosity. The yield was 68% which was far higher than that obtained by the conventional processes. When the obtained oily polysilazane was left to stand at room temperature, it turned into a glassy solid in 10 min. Thus, it was confirmed that the product was suitable for the shaping at room temperature.

COMPARATIVE EXAMPLE 1

The same apparatus as in Example 1 was used. 150 ml of dry degassed dichloromethane was placed in the four-necked flask. After cooling with ice, 16.1 g of dichlorosilane was added thereto. A gaseous mixture of 10.9 g of purified ammonia and nitrogen was introduced into the resulting solution under cooling with ice for 1 h. A dust was formed in the gas duct in the course of the reaction and, therefore, the duct was tapped at intervals to prevent the clogging.

The reaction mixture was treated in the same manner as in Example 1 to obtain 3.3 g of a viscous, oily polysilazane. The yield was 46% which was far lower than that obtained by the process of the present invention. The obtained polysilazane had a molecular weight of as low as 552 as determined by the vapor pressure osmometry and a low viscosity and, therefore, 2 to 5 days were necessitated for the solidification at room temperature. Thus, the shaping of the product at room temperature was difficult unlike the present invention.

EXAMPLE 3

A concentrated solution of the polysilazane obtained in Example 1 in dichloromethane was extruded through a nozzle into a vessel kept at 25° C. in a nitrogen atmosphere to obtain a short fibrous product. The product was kept at 25° C. under reduced pressure for 3 h to remove the solvent and to obtain a fibrous polysilazane.

EXAMPLE 4

0.3 g of the fibrous polysilazane obtained in Example 3 was heated to 120° C. in a nitrogen stream in a tubular aluminum oxide furnace and then to 1100° C. in 1 h. The polysilazane was kept at that temperature for 4 h. After leaving to cool to room temperature, the resulting product was in the form of light brown fibers. The product was silicon nitride having a silicon content of 39.5%, a chlorine content of up to 0.001% and an α-phase content of 80% as determined by powder X-ray diffraction.

From the above-mentioned results, it was proved that the inorganic polysilazane produced by the present invention can be shaped easily at room temperature to obtain an utterly new, shaped, sintered silicon nitride.

This invention has been described in detail with reference to the preferred embodiments thereof. However, it will be appreciated that those skilled in the art, upon consideration of this disclosure, may make obvious modifications and improvements within the spirit and scope of the invention and such modifications and improvements are intended to be within the scope of the hereto appended claims.

What we claim is:

1. Method for producing an inorganic polysilazane having at least a skeletal structure of the formula $(-SiH_2NH-)_n$ wherein n represents a numeral of at least 15 and a molecular weight of at least 690 comprising reacting a halosilane with a base other than ammonia to form a halosilane adduct and reacting the adduct with ammonia in an unreactive solvent, said base being selected from the group consisting of tertiary amines, sterically hindering-group containing secondary amines, phosphine, stibine, arsine, trimethylphosphine, dimethylphosphine, methyldiethylphosphine, triethylphosphine, trimethylarsine, trimethylstibene, trimethylamine, triethylamine, thiophene, furan, dioxane, selenophene and 1-methylphosphole.

2. Method according to claim 1, in which the base is less basic than ammonia.

3. Method according to claim 1, in which the base is pyridine, picoline, trimethylphosphine, dimethylethylphosphine, methyldiethylphosphine, triethylphosphine, thiophene, furan, dioxane, selenophene or 1-methylphosphole.

4. Method according to claim 1, in which the base is pyridine or picoline.

5. Method according to claim 1, in which the halosilane is a dihalosilane.

6. Method according to claim 5, in which the dihalosilane is of the general formula $SiH_2X_2$ or $Si_2H_4X_2$ in which X is F, Cl, Br or I.

7. Method according to claim 6, in which the dihalosilane is dichlorosilane.

8. Method according to claim 6, in which the base is pyridine or picoline.

9. Method according to claim 6, in which the molar ratio of base to silane is at least 2:1.

10. Method according to claim 6, in which the solvent is hexane, benzene, pyridine, chloromethane, ether or acetonitrile.

11. Method according to claim 6, in which the solvent is pyridine or chloromethane.

12. An inorganic polysilazane having a number average molecular weight between 690 and 2,000 and being soluble in at least one solvent and readily solidifiable after removal of the solvent.

13. An inorganic polysilazane according to claim 12, wherein said solvent contains at least one of hexane, benzene, pyridine, chloromethane, ether and acetonitrile.

14. An inorganic polysilazane having a number average molecular weight between 690 and 2,000 and being soluble in at least one solvent and readily solidifiable after removal of the solvent, said polysilazane being manufactured by reacting a holosilane with a base other than ammonia to form a halosilane adduct and reacting the adduct with ammonia in an unreactive solvent, said base being selected from the group consisting of tertiary amines, sterically hindering-group containing secondary amines, phosphine, stibine, arsine trimethylphosphine, dimethylphosphine, methyldiethylphosphine, triethylphosphine, trimethylarsine, trimethylstibene, trimethylamine, triethylamine, thiophene, furan, dioxane, selenophene and 1-methylphosphole.

15. An inorganic polysilazane according to claim 14, in which the base is less basic than ammonia.

16. An inorganic polysilazane according to claim 14, in which the base is pyridine, picoline, trimethylphosphine, dimethylethylphosphine, methyldiethylphosphine, triethylphosphine, thiophene, furan, dioxane, selenophene or 1-methylphosphole.

17. An inorganic polysilazane according to claim 14 in which the base is pyridine or picoline.

18. An inorganic polysilazane according to claim 14, in which the halosilane is a dihalosilane.

19. An inorganic polysilazane according to claim 18, in which the dihalosilane is of the general formula $SiH_2X_2$ or $Si_2H_4X_2$ in which X is F, Cl, Br or I.

20. An inorganic polysilazane according to claim 19, in which the dihalosilane is dichlorosilane.

21. An inorganic polysilazane according to claim 19, in which the base is pyridine or picoline.

22. An inorganic polysilazane according to claim 19, in which the molar ratio of base to silane is at least 2:1.

23. An inorganic polysilazane according to claim 19, in which the solvent is hexane, benzene, pyridine, chloromethane, ether or acetonitrile.

24. An inorganic polysilazane according to claim 19, in which the solvent is pyridine or chloromethane.

* * * * *